United States Patent [19]

Boos

[11] Plant 4,984

[45] Feb. 22, 1983

[54] NECTARINE TREE

[76] Inventor: Albert A. Boos, 6947 S. Reed Ave., Reedley, Calif. 93654

[21] Appl. No.: 293,302

[22] Filed: Aug. 17, 1981

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is medium in size, vigorous, and upright-spreading; foliated with medium size, lanceolate leaves having a crenate to finely serrate margin, a medium length petiole, and medium size, reniform, alternate glands positioned on base of the leaf blade; flowers from hardy, pointed, medium size buds free from the stem and moderately pubescent; the flowers, blooming in medium season, being large, showy, and pink; and is a regular and productive bearer of late in mid-season, uniform, large, broadly ovoid, freestone fruit having yellow skin substantially entirely blushed with a waxy bright red, yellow flesh flecked and mottled with red, and a dark brown stone.

1 Drawing Figure

BACKGROUND OF THE VARIETY

FIELD OF THE INVENTION

In the course of the maintenance of a nectarine orchard on my ranch located near Reedley, Fresno County, Calif., I frequent such orchard for the purpose of inspection, cultivation, and irrigation, and — during the course of such activities — I am aware of the condition of the trees and recognize any other-than-normal growth characteristics of them. It was under such conditions that the present variety of nectarine tree was discovered by me.

CLASSIFICATION OF THE VARIETY

The present new and distinct variety of nectarine tree is embraced by Class 41, Plants, of the United States Patent Office Manual of Classification.

PRIOR VARIETIES

Among existing varieties of nectarine trees which are known to me, and mentioned herein, is the Fantasia (unpatented).

ORIGIN OF THE VARIETY

The present variety of nectarine tree was discovered by me, in an orchard on my ranch located as aforesaid, as a full scaffold limb on a mature tree of the Fantasia variety. Upon close and continued observation of such scaffold limb, I confirmed my initial realization that it had certain novel and distinctive crop characteristics in comparison with the remainder of the host tree. I, therefore, determined to effect asexual reproduction of the variety as represented by such full scaffold limb.

ASEXUAL REPRODUCTION OF THE VARIETY

The present variety of nectarine tree was asexually reproduced, by grafting on compatible rootstock, on my ranch located as aforesaid; such reproductions having been successful, and, in maturity, ran true in all respects.

SUMMARY OF THE VARIETY

The present variety of nectarine tree is — characteristically — medium in size, vigorous, and upright-spreading; foliated with medium size, lanceolate leaves having a crenate to finely serrate margin, a medium length petiole, and medium size, reniform, alternate glands positioned on base of the leaf blade; flowers from hardy, pointed, medium size buds free from the stem and moderately pubescent; the flowers, blooming in medium season, being large, showy, and pink; and is a regular and productive bearer of late in mid-season, uniform, large, broadly ovoid, freestone fruit having yellow skin substantially entirely blushed with a waxy bright red, yellow flesh flecked and mottled with red, and a dark brown stone.

The present variety of nectarine tree — while generally similar to the Fantasia in tree characteristics, regular bearing habit, and large fruit size — is particularly distinctive, in comparison, by fruit in harvest approximately two weeks later, by fruit which possesses a more attractive, waxy, bright red blush color, and by fruit of superior firmness of flesh and toughness of skin.

BRIEF DESCRIPTION OF THE DRAWING

The drawing is an illustration, by photographic reproduction in color, of separate fruit of the variety, together with a fragmentary view of leaves; one fruit being halved to expose the flesh and with the stone remaining in one half.

DESCRIPTION OF THE VARIETY

The botanical details of this new and distinct variety of nectarine tree — with color definitions (except those in common color terms) referenced to Maerz and Paul Dictionary of Color (1950 edition) — are as follows:

Tree:
- *Size.*—Medium.
- *Vigor.*—Vigorous.
- *Growth.*—Upright-spreading.

Trunk:
- *Size.*—Medium.
- *Texture.*—Smooth to medium.
- *Color.*—Gray (7-C-8).

Branches:
- *Size.*—Medium.
- *Texture.*—Medium.

*Color.*—Current season's shoots: Light green (19-J-5) with some areas tinged red where exposed to sunlight. Young wood: Brownish (8-C-11). Mature wood: Brownish gray (8-A-9).

*Lenticels.*—Average number and size.

Leaves:

*Size.*—Medium. Average length — 14.5 cm. Average width — 3.7 cm.

*Form.*—Lanceolate. Apex — acuminate.

*Thickness.*—Medium.

*Texture.*—Moderately smooth.

*Color.*—Top Side — Medium green (23-L-8). Under Side — Lighter green (21-J-7).

*Margin.*—Crenate to finely serrate. Slightly wavy.

*Petiole.*—Medium length (average 8–10 mm.). Medium thickness. Light green (20-I-6).

*Glands.*—Medium size. Reniform. Number — 2–4 (variable). Commonly alternate in position at base of leaf blade. Light green to yellow — green on young foliage.

*Stipules.*—Medium size. Narrow. Early deciduous.

Flower buds:

*Hardiness.*—Hardy for California conditions.

*Size.*—Medium.

*Length.*—Medium.

*Form.*—Pointed. Free from stem.

*Pubescence.*—Moderate.

Flowers:

*Blooming period.*—Date of first bloom: Feb. 23, 1981. Date of full bloom: Mar. 7, 1981. Medium, as compared with other varieties. Nearly identical with Fantasia.

*Size.*—Large. Showy. Normally 1–2 per node. 43–48 mm. in diameter when fully open. Average petal length — 22.4 mm. Average petal width — 19.1 mm. Petal edges slightly irregular and usually somewhat wavy.

*Color.*—Light pink (49-B-3) — slightly lighter along outer edge of petals.

*Stamens.*—Average number — 40. Average length — 11–14 mm.

*Calyx lobes.*—6–7 mm. long. 5–6 mm. wide.

*Anthers.*—Yellow, edged in red.

*Nectarines.*—Greenish orange — variable.

Fruit:

*Maturity when described.*—Firm commercial maturity — Aug. 1, 1980.

*Date of first picking.*—July 27, 1980.

*Date of last picking.*—Aug. 10, 1980.

*Size.*—Uniform. Large. Average cheek diameter — 72.0 mm. Average suture diameter — 67.0 mm. Average axial length — 72.7 mm.

*Form.*—Uniform. Nearly symmetrical in ventral suture aspect. Broadly ovoid.

*Suture.*—Ventral suture a broad relatively deep distinct line extending from base to apex, discontinuous at apex, but then a broad shallow depression from apex to base throughout dorsal suture.

*Ventral surface.*—Rounded. Moderately lipped throughout length of suture on both sides.

*Lips.*—Variable. Most commonly slightly unequal.

*Stem cavity.*—Axial aspect rounded to very slightly elongated in suture plane. Average length — 16.0 mm. Average width — 13.0 mm. Conic. Average depth — 11.5 mm.

*Stem.*—Medium length — (average — 11.8 mm.).

*Base.*—Rounded to occasionally oblique to either edge.

*Apex.*—Short. Slight tip.

*Pistil point.*—Variable, but usually oblique.

Skin:

*Thickness.*—Thick.

*Texture.*—Moderately tough.

*Tenacity.*—Tenacious to flesh at commercial maturity.

*Tendency to crack.*—None observed.

*Color.*—Ground color — Yellow. Blush color — Orange-red (3-L-10) to Garnet red (6-L-5).

*Pubescence.*—Wanting.

Flesh:

*Color.*—Yellow (10-J-7) mottled with red. Surface of pit cavity: Red, with pink to red fibers.

*Amygdalin.*—Wanting.

*Juice.*—Moderate.

*Texture.*—Firm. Crisp.

*Fibers.*—Few. Tender.

*Ripens.*—Evenly.

*Flavor.*—Mild. Well balanced.

*Aroma.*—Distinct. Mild.

*Eating quality.*—Good.

Stone:

*Type.*—Free. Occasionally adheres to flesh at base of ventral suture. Fibers — moderately long. Parts from flesh smoothly.

*Size.*—Medium. Average length — 38.8 mm. Average breadth — 26.5 mm. Average thickness — 19.9 mm.

*Form.*—Roughly obovoid. Somewhat irregular in lateral aspect, with dorsal ridge moderately recurved near apex.

*Base.*—Very slightly oblique to ventral edge.

*Hilum.*—Oval.

*Apex.*—Acuminate. Tip usually quite sharp, but occasionally truncated.

*Sides.*—Slightly unequal, at times curved either right or left, or nearly straight.

*Surface.*—Lateral channels deep near apex. Irregularly furrowed along both dorsal and ventral edges. Pitted from base to slightly below center.

*Ridges.*—Jagged throughout.

*Pits.*—Circular to elongated (variable in shape).

*Ventral edge.*—Moderately thick. Eroded throughout, with low wings converging apically.

*Dorsal edge.*—Full, with deep, broad groove extending from base to well above center. Heavily eroded near apex.

*Color.*—Dark brown (7-E-10) with reddish stain (7-J-2) on base and lower dorsal and ventral suture.

*Tendency to split.*—Slight.

Use: Fresh shipping.

Keeping quality: Average.

Resistance to insects and diseases: No particular susceptibilities observed.

Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized in comparison with the Fantasia by fruit in harvest approximately two weeks later, by fruit having a more attractive, waxy, bright red blush color, and by fruit of superior firmness of flesh and toughness of skin.

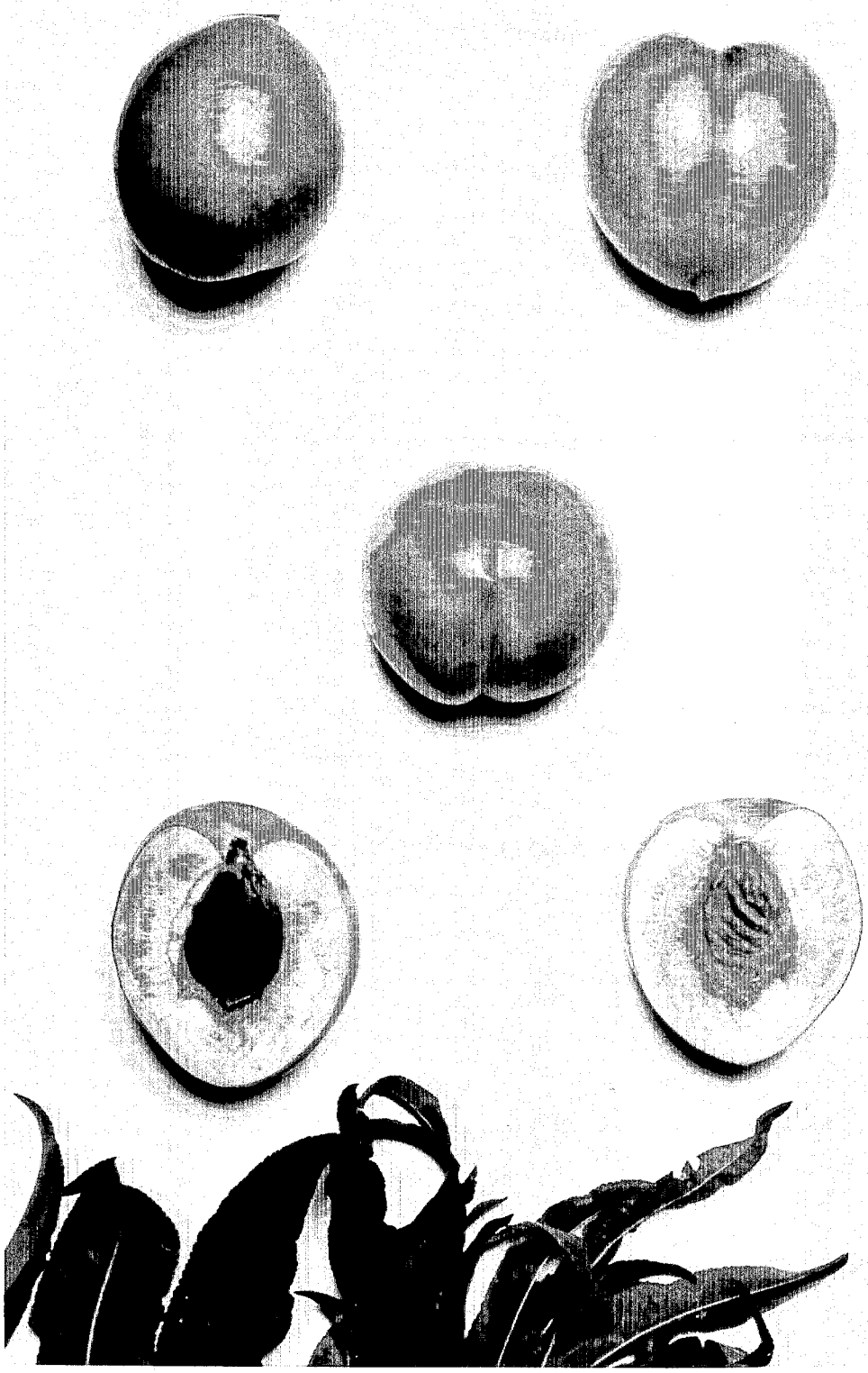

* * * * *